(12) United States Patent
Veeger et al.

(10) Patent No.: US 7,670,615 B2
(45) Date of Patent: Mar. 2, 2010

(54) ALCOHOLIC PUMP FOAM

(75) Inventors: Marcel Veeger, Goch (DE); Markus Himming, Oberhausen (DE)

(73) Assignee: Stockhausen GmbH, Krefeld (DE)

( * ) Notice: Subject to any disclaimer, the term of this patent is extended or adjusted under 35 U.S.C. 154(b) by 23 days.

(21) Appl. No.: 11/312,559

(22) Filed: Dec. 21, 2005

(65) Prior Publication Data

US 2006/0182690 A1 Aug. 17, 2006

(30) Foreign Application Priority Data

Dec. 21, 2004 (DE) .................. 10 2004 062 775

(51) Int. Cl.
*A01N 25/00* (2006.01)
*A01N 31/00* (2006.01)
*A01N 31/14* (2006.01)
*A01N 43/04* (2006.01)
*A01N 55/00* (2006.01)
*C11D 3/22* (2006.01)
*C11D 3/37* (2006.01)

(52) U.S. Cl. .................. 424/405; 514/25; 514/63; 514/715; 514/724; 514/738; 514/781; 510/473; 510/475

(58) Field of Classification Search .................. 424/45, 424/405; 510/130, 131, 138; 514/724
See application file for complete search history.

(56) References Cited

U.S. PATENT DOCUMENTS

| | | | | |
|---|---|---|---|---|
| 3,963,507 | A * | 6/1976 | Kuramoto et al. ............. | 521/83 |
| 4,511,486 | A | 4/1985 | Shah | |
| 4,714,568 | A * | 12/1987 | Hurnik et al. ................. | 516/11 |
| 5,122,541 | A | 6/1992 | Eggensperger et al. | |
| 5,167,950 | A | 12/1992 | Lins | |
| 5,902,778 | A * | 5/1999 | Hartmann et al. ........... | 510/135 |
| 6,376,438 | B1 | 4/2002 | Rosenberger et al. | |
| 6,383,997 | B1 | 5/2002 | McManus | |
| 6,471,983 | B1 | 10/2002 | Veeger et al. | |
| 6,489,275 | B1 | 12/2002 | Veeger et al. | |
| 7,163,916 | B2 | 1/2007 | Allef et al. | |
| 7,241,452 | B2 | 7/2007 | Veeger et al. | |
| 7,297,675 | B2 | 11/2007 | Allef et al. | |
| 2002/0127253 | A1 | 9/2002 | Scholz et al. | |
| 2004/0170592 | A1 | 9/2004 | Veeger et al. | |
| 2004/0191274 | A1 | 9/2004 | Grayson et al. | |
| 2005/0031580 | A1 | 2/2005 | Allef et al. | |
| 2005/0129626 | A1 | 6/2005 | Koivisto et al. | |
| 2005/0226838 | A1 | 10/2005 | Krause et al. | |
| 2006/0165627 | A1 | 7/2006 | Allef et al. | |
| 2006/0198859 | A1 | 9/2006 | Allef et al. | |
| 2006/0204468 | A1 | 9/2006 | Allef et al. | |
| 2007/0027055 | A1 * | 2/2007 | Koivisto et al. ............. | 510/383 |
| 2007/0041927 | A1 | 2/2007 | Blaeser et al. | |
| 2007/0065383 | A1 * | 3/2007 | Fernandez de Castro et al. ............. | 424/70.1 |
| 2007/0092470 | A1 | 4/2007 | Allef et al. | |
| 2007/0179207 | A1 * | 8/2007 | Fernandez de Castro et al. ............. | 521/99 |
| 2007/0258911 | A1 * | 11/2007 | Fernandez de Castro et al. ............. | 424/47 |
| 2008/0145320 | A1 | 6/2008 | Wenk et al. | |
| 2008/0305056 | A1 | 12/2008 | Jenni et al. | |
| 2009/0054521 | A1 | 2/2009 | Herrwerth et al. | |

FOREIGN PATENT DOCUMENTS

| | | |
|---|---|---|
| CA | 2 587 086 A1 | 4/2006 |
| DE | 28 52 593 C2 | 6/1979 |
| DE | 33 06 593 A1 | 9/1983 |
| DE | 695 12 841 T2 | 5/2000 |
| DE | 696 30 221 T2 | 7/2004 |
| EP | 0 160 051 B1 | 11/1985 |
| EP | 0 384 126 | 8/1990 |
| EP | 0 689-767 A2 | 1/1996 |
| EP | 1 584 323 A1 | 10/2005 |
| EP | 1967576 A1 | 9/2008 |
| GB | 1 010 874 A | 7/1979 |
| WO | WO 93/07250 | 4/1993 |
| WO | WO 97/00668 | 1/1997 |
| WO | WO 03/028671 A2 | 4/2003 |
| WO | 2005/123012 A1 | 12/2005 |
| WO | 2006/042588 A1 | 4/2006 |

OTHER PUBLICATIONS

Degussa: Goldschmidt Personal Care, Catalogue of Products, p. 30, Oct. 2004.*

(Continued)

*Primary Examiner*—Johann R Richter
*Assistant Examiner*—Nathan W Schlientz
(74) *Attorney, Agent, or Firm*—Oblon, Spivak, McClelland, Maier & Neustadt, L.L.P.

(57) ABSTRACT

An alcoholic foam composition, which can be dispensed as a foam via a pump-foam system contains a) at least 52 to ≦99 wt % of an alcohol or mixture of alcohols, b) a surfactant or a surfactant mixture, c) at least one polyalkylene glycol, d) optionally, at least one foam stabilizer, e) optionally, at least one member selected from the group consisting of cosmetic auxiliaries, adjuvants, active ingredients, and mixtures thereof, and f) optionally water. The surface tension of component b) lies in the range of ±15 dyn/cm of the surface tension of component a) or corresponds to the surface tension of component a), and the sum of components a) to f) is 100 wt % relative to the total quantity of the foam composition.

12 Claims, No Drawings

OTHER PUBLICATIONS

S. C. Crema, et al., "Foaming of Anhydrous Methanol for Well Stimulation", Society of Petroleum Engineers, SPE 13565, (1985).
Paul A. Sanders, "Aqueous Alcohol Aerosol Foams", Drug & Cosmetic Industry, XP000960450, vol. 99, No. 2, 1966, pp. 56, 58, 60, 142, 143, 146-154.
Patent Abstracts of Japan—English Abstract of 07285808 A (application No. 05343940, filed Dec. 18, 1993).
Patent Abstracts of Japan—English Abstract of 06279268 A (application No. 06022166, filed Jan. 21, 1994).
Patent Abstracts of Japan—English Abstract of 11349418 A (application No. 10159268, filed Jun. 8, 1998).
esp@cenet—English Abstract of EP0384126.
esp@cenet—English Abstract of DE69512841T.
esp@cenet—English Abstract of DE2852593.
esp@cenet—English Abstract of DE3306593.
esp@cenet—English Abstract of DE69630221T.
U.S. Appl. No. 12/514,326, filed May 11, 2009, Veeger, et al.

* cited by examiner

ALCOHOLIC PUMP FOAM

BACKGROUND OF THE INVENTION

1. Field of the Invention

The present invention relates to alcoholic foam compositions.

2. Discussion of the Background

Disinfectants are used to combat pathogenic microorganisms such as bacteria, viruses, spores, fungi, etc. The use of disinfectants is unavoidable in many regions or the use is expressly required by the legislators in many countries.

Disinfectants are usually classified according to their area of application and, depending on intended use, a distinction is made between antiseptics for wound, skin, stools and sputum disinfection as well as instruments disinfection, laundry and surface disinfectants, and especially also skin and hand disinfectants.

The area of application of the aforesaid disinfectants is medically indicated and they are used for prevention of infections in hospitals, doctors' and dentists' offices, in public areas such as schools, kindergartens, nursing institutions, retirement homes, sanatoriums, etc., and also in sports facilities and other places in which infections can be transmitted. Besides the use of disinfectants in the food industry and pharmaceutical industry, they are in general use not only at the workplace or in the home, but also in service industries such as laundries and kitchens, where the products are delivered directly to patients or consumers.

Demonstration of the effectiveness of such disinfecting agents for one or more of the aforesaid areas of applications is achieved by thorough testing of these agents on the basis of standardized test methods, such as the guidelines of the German Association for Hygiene and Microbiology (DGHM) in Germany or the guidelines of the French Association for Standardization (AFNOR) in France. Examples of further standards are listed below:

| | |
|---|---|
| DIN EN 1040 | Chemical disinfectants and antiseptics (basic test) |
| DIN EN 1276 | Chemical disinfectants and antiseptics Bactericidal action in the fields of foods, industry, home and public institutions |
| DIN EN 1499 | Disinfecting hand washing |
| DIN EN 1500 | Hygienic hand disinfection |
| DIN EN 12054 | Chemical disinfectants and antiseptics Products for hygienic and surgical hand disinfection and hand washing - bactericidal effect |
| DIN EN 12791 | Surgical hand disinfectants |
| AFNOR T 72 300 | Bactericidal effectiveness of antiseptics and disinfectants that are employed as liquid mixed in water |
| AFNOR T 72 170 | Bactericidal effectiveness in the presence of interfering substances |
| NF EN 1040 | Bactericidal effectiveness of antiseptics and chemical disinfectants |
| NF EN 1275 | Fungicidal effectiveness of antiseptics and chemical disinfectants |

In the capacity of pharmaceuticals, antiseptics are further subject to legally governed approval and registration procedures.

For example, as can be seen from German Patent DE 4328828 A, various methods are available for achieving hand disinfection. Explicitly mentioned therein are the alcoholic hand disinfection methods that are standard in Germany as well as the scrub methods of hand disinfection. Products intended for hand disinfection among other purposes must satisfy at least the minimum requirements indicated in the aforesaid standards if they are to be certified as conforming with those standards and included as preparations in the disinfection list of the DGHM.

Commercially available disinfectants, especially skin and hand disinfectants, are usually composed of alcohol or mixtures of alcohols, optionally of active ingredients, which remain on the skin after evaporation of the alcohol components and which can be, for example, nonvolatile antimicrobial substances and/or common skin-care substances, and possibly other auxiliaries. If the alcohol component is used alone as the antimicrobial agent, the alcohol concentration in the product is to be chosen such that a disinfectant effect is assured even after evaporation of part of the alcohol. In this connection, it is known that this is the case for ethanolic compositions having an alcohol concentration of at least 52 wt %.

To address the disadvantages of alcoholic disinfectant solutions applied for skin and hand disinfection, thickeners have been added to such disinfectant solutions in order to increase the viscosity of these agents. Disadvantages include especially the difficulty of dosing due to the fact that the needed quantity of disinfectant often cannot be distributed uniformly over the skin or the hands and that aqueous alcohol solutions drip very easily from the hands. An example for added thickeners is found in European Patent EP 0604848 B, wherein the subject matter is a fast-drying disinfectant composition. As thickener there is described a combination of carboxyvinyl polymers and hydroxypropylmethylcellulose, wherein the total weight of the two components in the disinfectant composition is not greater than 3 wt %.

Also known are antimicrobial alcoholic gel compositions for skin and hand disinfection containing moisturizers and skin-care substances, as described in, for example, U.S. Pat. No. 4,956,170. In these compositions, cross-linked partly neutralized or neutralized acrylic acid polymers are used as thickeners. The antibacterial agent used in these compositions is 60 to 75 wt % of alcohol such as ethanol, isopropyl alcohol or mixtures thereof. Regarding the emollients contained in these gel compositions, especially petrolatum and other mineral-oil products that can be used in cosmetic preparations, as well as further hydrophobic constituents that can be used safely not only in cosmetics but also in disinfectants, it has been found that the use of such constituents in alcoholic gel compositions having high alcohol concentrations is highly detrimental to the stability of such gels, because the gels lose their viscosity and therefore their stability in the course of time during storage, and the compositions deliquesce. In general, it has been found that the gel stability suffers with increasing alcohol concentration, especially at alcohol concentrations higher than 60 wt %.

Such high alcohol concentrations, especially in gel compositions containing alcohol as the sole active component, are unavoidable, however, in order that such agents can also be certified as disinfectants for hand disinfection.

German Patent DE 10132382 discloses a simple, economic production method for the production of stable disinfectant hand-care and skin-care gels having high alcohol concentration, permitting the production of disinfectant hand-care gels that contain care components, that satisfy the standards

| | |
|---|---|
| DIN EN 1499 | Disinfecting hand washing |
| DIN EN 1500 | Hygienic hand disinfection | among others directly without further additional antimicrobial adjuvants, and that also have a hepatitis B activity. Although it has been shown that the application of a disinfectant agent in gel form is to be preferred to the application of a disinfectant agent in liquid form, especially as regards its drying-out tendency, such disinfectant alcoholic gel compositions nevertheless have the disadvantage that they must lose their gel structure upon being applied on the skin, in order to ensure uniform wetting of the skin areas and thus a safe disinfectant action.

Also known are alcoholic cleaning foam compositions, which are dispensed by commercially available pump-foam systems, which are to be found mainly in sanitary units of hospitals, doctors' and dentists' offices, schools, kindergartens and nursing institutions, such as old-age homes, sanatoriums, etc. The alcohol concentration of such foam compositions is only around 40 wt %, however, because the instability of the foams increases at higher alcohol concentrations. This can also be regarded as the reason why the advantageous form of application by means of foam, which is even more manageable than alcoholic gels, has not yet been considered for disinfectants, especially not for skin and hand disinfection, because of the low alcohol concentration of the products that have been commercially available heretofore.

SUMMARY OF THE INVENTION

It is an object of the present invention to provide an alcoholic foam composition that can be dispensed as pump foam, particularly via standard pump-foam systems, to the consumer for disinfection purposes, preferably for skin and hand disinfection.

It is another object of the present invention to provide an alcoholic foam that is stabilized in such a way that alcoholic foam having an alcohol concentration of at least 52 wt %, especially greater than 60 wt % of alcohol can be dispensed in order to ensure safe disinfection, especially skin and hand disinfection.

This and other objects have been achieved by the present invention the first embodiment of which includes an alcoholic foam composition, comprising:
  a) at least 52 to $\leq 99$ wt %, relative to the total quantity of the foam composition, of an alcohol or mixture of alcohols,
  b) a surfactant or a surfactant mixture,
  c) at least one polyalkylene glycol,
  d) optionally, at least one foam stabilizer,
  e) optionally, at least one member selected from the group consisting of cosmetic auxiliaries, adjuvants, active ingredients, and mixtures thereof, and
  f) optionally water,
wherein the surface tension of component b) lies in the range of $\pm 15$ dyn/cm of the surface tension of component a) or corresponds to the surface tension of component a), and
wherein the sum of components a) to f) is 100 wt % relative to the total quantity of the foam composition.

DETAILED DESCRIPTION OF THE INVENTION

The present invention provides an alcoholic foam composition for disinfection, especially a pump-foam formulation, which contains the components
  a) at least 52 to $\leq 99$ wt %, relative to the total quantity of the foam composition, of an alcohol or mixture of alcohols,
  b) a surfactant or a surfactant mixture,
  c) at least one polyalkylene glycol,
  d) optionally, at least one foam stabilizer,
  e) optionally, at least one member selected from the group consisting of cosmetic auxiliaries, adjuvants, active ingredients, and mixtures thereof, and
  f) optionally water,
wherein the surface tension of component b) is in the range of $\pm 15$ dyn/cm of the surface tension of component a) or corresponds to the surface tension of component a), and the sum of components a) to f) is 100 wt % relative to the total quantity of the foam composition. In other words, the surface tension of component b) is in the range of not less than about 15 dyn/cm below the surface tension of component a) and not more than about 15 dyn/cm above the surface tension of component a).

It was completely surprising that such alcoholic foam compositions, which preferably are suitable for skin and hand disinfection and which contain at least 52 wt % relative to the total quantity of the foam composition, can be dispensed as foam via standard pump-foam systems, without suffering spontaneous foam breaking because of the high alcohol concentration in the composition. In particular, it would have been expected of such high alcohol concentrations that the alcohol components of such foam compositions would act merely as a solvent at an alcohol concentration of higher than 50 wt %, whereby the surface-active effects of the surfactants and accordingly their foaming ability also would be lowered. Such effects were not observed, however. To the contrary, it was found that stable voluminous foams for disinfection purposes could be produced with the foam compositions according to the present invention in standard pump-foam systems.

According to the present invention, the surface tension of component b) preferably lies in the range of $\geq 20$ to $\leq 40$ dyn/cm. The surface tension of component b) includes all values and subvalues therebetween, especially including 22, 24, 26, 28, 30, 32, 34, 36 and 38 dyn/cm.

Preferably, the alcoholic foam composition contains, as component a), alcohols of the general formula

in which R denotes an aliphatic straight-chain or branched hydrocarbon group that has 1 to 8 carbon atoms and that can be contained alone or in mixtures in the foam according to the present invention.

Examples of such alcohols are methanol, ethanol, 1-propanol, 2-propanol, 1-butanol, isobutyl alcohol, tert-butyl alcohol, the amyl alcohols, 1-, 2-, 3-pentanol or neopentyl alcohol as well as 1-hexanol, ethanol being particularly preferred as component a).

Preferably, the foam composition contains at least 52 to 99 wt %, preferably 55 to 96 wt % and especially more than 65 wt % of ethanol. The amount of ethanol includes all values and subvalues therebetween, especially including 55, 60, 65, 70, 75, 80, 85, 90 and 95 wt %. As regards the disinfectant action, it is particularly advantageous for the alcoholic foams according to the present invention to contain more than 80 wt % of alcohol.

As component b), the foam compositions according to the present invention can contain respectively a surfactant or surfactant mixture, with the proviso that the surface tension of the surfactant or of the surfactant mixture contained in the foam composition lies within the range of $\pm 15$ dyn/cm of the surface tension of component a), meaning the alcohol component, or corresponds to the surface tension of component a).

Every surfactant or surfactant mixture that satisfies the foregoing proviso is suitable as component b) of the foam compositions. The total quantity of the surfactant or surfactant mixture is 0.5 to 20, preferably 1 to 10 and particularly preferably 2 to 5 wt % relative to the total quantity of the foam composition. The amount of surfactant or surfactant mixture includes all values and subvalues therebetween, especially including 1, 2, 4, 6, 8, 10, 12, 14, 16, and 18 wt %.

Such surfactants are, among other substances, silicone compounds, such as dimethylpolysiloxanes, methylphenylpolysiloxanes, cyclic silicones as well as silicone compounds modified by amino, fatty acid, alcohol, polyether, epoxy, fluoro, glycoside and or alkyl groups. Preferred as silicone compounds according to the present invention are polysiloxane-polyether copolymers [INCI(CFTA): dimethicone copolyol], which are available from the company named Goldschmidt AG of Essen under the trade name ABIL®, especially polysiloxane-polyether copolymers of the B 88 product family, such as ABIL® B 8843, ABIL® B 8851, ABIL® B 8852, ABIL® B 8863, ABIL® B 88183 and ABIL® B 88184. Particularly preferably, the foam compositions according to the present invention contain, as component b), polysiloxane-polyether copolymers available under the trade name ABIL® B 8832 (bis-PEG/PPG-20/20 dimethicone).

As further suitable surfactants or surfactant mixtures there can be mentioned the group of fluoro surfactants, which can be present as component b) in the foams, either alone or as mixture of various fluoro surfactants, especially also as mixtures with polysiloxane-polyether copolymers. Such suitable surfactants are, for example, tetraalkylammonium perfluoroalkylsulfonates, preferably the tetraethylammonium perfluorooctanesulfonate that is commercially available under the trade name FLUORTENSIDE FT-248.

Furthermore, the foam compositions contain, as component c), at least one polyalkylene glycol, which can be present preferably in proportions of 0.01 to 3, especially 0.01 to 0.2 and particularly preferably 0.05 to 0.2 wt % relative to the total quantity of the foam composition. The amount of polyalkylene glycol includes all values and subvalues therebetween, especially including 0.05, 0.1, 0.5, 1, 1.5, 2, and 2.5 wt %. Preferred polyalkylene glycols according to the present invention are in particular polyethylene oxide homopolymers with a molecular weight of 100,000 to 8,000,000, which are available as commercial products on the market under the trademark Polyox®, such as Polyox® WSR N-10, Polyox® WSR N-80 (PEG-5M), Polyox® WSR N-750 (PEG-7M), Polyox® WSR N-3000 (PEG-14M), Polyox® WSR N-3333, Polyox® WSR-205 (PEG-14M), Polyox® WSR-1105, Polyox® WSR N-12K, Polyox® WSR N-60K (PEG-45M) and Polyox® WSR-301.

The foam compositions contain optionally at least one foam stabilizer, which is present as component d) in the foam in a proportion of 0.01 to 20 wt %, preferably 0.5 to 3 wt % relative to the total quantity of the foam composition. The amount of foam stabilizer includes all values and subvalues therebetween, especially including 0.05, 0.1, 0.5, 1, 2, 4, 6, 8, 10, 12, 14, 16 and 18 wt %. Examples of suitable foam stabilizers are polysaccharides, especially xanthan gum, guar-guar, agar-agar, alginates and tyloses, cellulose ethers, such as carboxymethylcellulose, ethylcellulose, hydroxypropylcellulose, methylcellulose, cellulose mixed ethers, such as carboxymethylhydroxyethylcellulose, ethylhydroxyethylcellulose, methoxyhydroxyalkylcelluloses, methylhydroxyalkylcelluloses, such as methylhydroxyethylcellulose, methylhydroxypropylcellulose, methylhydroxybutylcellulose. Preferred according to the present invention are alkylcelluloses, especially methylcellulose and ethylcellulose that are commercially available under the trade names METHOCEL® and ETHOCEL®, Besides water, the alcoholic foams according to the present invention can, if necessary, contain auxiliaries, adjuvants and/or active ingredients, such as dyes, solubilizers, complexing agents, sequestering agents, light-protecting filters or perfumes and scents, pH regulators, stabilizers, preferably cetearyl alcohol and/or hydrogenated castor oils, such as trihydroxystearin, preservatives, antioxidants and/or oil-based or water-based care components as component e), especially in standard proportions of preferably 0.05 to 5 wt % relative to the total weight of the foams. The amount of additional components includes all values and subvalues therebetween, especially including 0.05, 0.1, 0.5, 1, 1.5, 2, 2.5, 3, 3.5, 4 and 4.5 wt %. These optional constituents of component e) can normally be present in proportions of 0 to 5 wt % relative to the total weight of the foam, but the person skilled in the art will choose the weight proportion of component e) such that no impairment of foam formation occurs.

In a preferred embodiment of the present invention, the foams contain 55 to 96 wt % of ethanol, 1 to 10 wt % of bis-PEG/PPG-20/20 dimethicone as silicone surfactant, 0.0 to 3 wt % of ethylcellulose polymer as stabilizer in combination with a PEG polymer, selected from PEG 7M to PEG 45M, preferably 0.05 to 2 wt %, whereby very effectively disinfecting foams with excellent stability are obtained in standard pump-foam systems. These amounts are given based on the total weight of the foam composition. The amount of ethanol includes all values and subvalues therebetween, especially including 60, 65, 70, 75, 80, 85 and 90 wt %. The amount of bis-PEG/PPG-20/20 dimethicone includes all values and subvalues therebetween, especially including 0.1, 0.5, 1, 2, 3, 4, 5, 6, 7, 8 and 9 wt %. The amount of ethylcellulose polymer includes all values and subvalues therebetween, especially including 0.1, 0.5, 1, 1.5, 2 and 2.5 wt %. The amount of PEG polymer includes all values and subvalues therebetween, especially including 0.1, 0.5, 1, and 1.5 wt %.

The alcoholic foams according to the present invention can be used particularly advantageously as disinfectants, for example as antiseptics for wound, skin, stools and sputum disinfection as well as instrument disinfection, as laundry and surface disinfectants and, particularly preferably according to the present invention, as skin and hand disinfectants.

The possible optional addition of nonvolatile antimicrobial substances in the foams is used in particular to intensify the disinfectant properties of the alcohol component. Of course, this depends on the area of application for which the foams are intended.

Antimicrobial substances can be present if necessary and can be used in the foams preferably alone or as combinations of a plurality of disinfectant active ingredients. Preferred are invert soaps, such as cationic surfactants, quaternary ammonium compounds, including benzalkonium chlorides or benzethonium chloride, biguanide compounds, such as chlorhexidine salts, phenol compounds, cresols, per compounds, iodine compounds, such as polyvidone iodine, organic acids, etc.

Nevertheless, the addition of such antimicrobial active ingredients may not be not necessary, since the foams have such a high alcohol concentration that the alcohol component functions as the disinfectant active ingredient on its own.

According to the present invention, care and/or moisturizing active ingredients, which can be contained optionally in the foams, especially for use of the foams as skin and hand disinfectants, are active ingredients that remain on the skin after evaporation of the alcohol component of the foam, for example standard skin-care substances such as dexpanthenol, glycerin, 1,2-propanediol, sorbitol, 1,3-butylene glycol, polyethylene glycol and other polyalcohols, hyaluronic acids, urea, chamomile extracts, alkoxylated cetyl alcohols and/or nonvolatile antimicrobial substances.

Since, during use as skin and hand disinfectants, the high alcohol proportion in the foams causes drying out of the treated skin areas during application, the use of at least one skin-care substance and/or one moisturizer is actually indispensable in daily practice with regard to frequent application of such disinfectants.

Also advantageous for the use of the foams for skin and hand disinfection is a constituent of natural plant tannins, such as ladies' mantle (*Alchemilla xanthochlora*, Rosaceae), tormentil rootstock (*Potentilla erecta*, Rosaceae), oak bark (*Quercus petraea* and *Quercus robur*, Fagaceae), ratanhia root (*Krameria lappacea* syn. *K. triandra*, Krameriaceae), witch hazel leaves (*Hamamelis virginiana*, Hamamelidaceae) and bilberries (*Vaccinium myrtillus*, Ericaceae) and natural synthetic tannins, such as Na bichlorophenylsulfamine, preferably in a proportion of 0.01 to 5 wt % of active substance relative to the total quantity of the foams. Of those, *Hamamelis virginiana* is particularly preferred as tannin. The amount of tannin includes all values and subvalues therebetween, especially including 0.05, 0.1, 0.5, 1, 1.5, 2, 2.5, 3, 3.5, 4 and 4.5 wt %.

Despite their high alcohol concentration, the foams are characterized by very good stability, and so stable disinfectant foams, especially for skin and hand disinfection, are made available by the present invention. Even without further additional antimicrobial adjuvants, these foams satisfy the standards

| DIN EN 1499 | Disinfecting hand washing |
| DIN EN 1500 | Hygienic hand disinfection | among others, and in addition have hepatitis B activity. The latter effect especially is particularly advantageous, since the hepatitis B virus, just as the HIV virus that is responsible for the spread of AIDS (acquired immune deficiency syndrome), is communicable but is more stable and more infectious than the HIV virus. Thus, all precautions against transmission of hepatitis B are also preventive against the HIV virus (see Deutsches Ärzteblatt 84, No. 18, p. B 874 of 30 Apr. 1987).

Since the foams according to the present invention can have alcohol concentrations of >70 vol % or 60 wt % relative to the total quantity of the foam, they also have virus activity against "naked" or nonenveloped viruses, such as polioviruses and adenoviruses, and so such alcoholic foams are of particular interest as a form of application, especially for skin disinfection.

It is also advantageous that the foams according to the present invention can be dispensed in particular as pump foams via standard pump-foam systems to the consumers for disinfection purposes, preferably for skin and hand disinfection, especially because such pump foams can usually be manufactured inexpensively and simply as aerosol-base foams. Examples include the commercially available pump-foam systems of companies such as Airspray (Netherlands), Keltec (Netherlands), Ophardt (Germany), Brightwell (United Kingdom) and Supermatic (Switzerland).

The foam compositions of the present invention can be obtained by mixing components a) to c) and optionally d), e) and/or f).

Foam compositions preferred according to the present invention (all data in wt % relative to the total quantity of the foam composition):

| | Example | | | | |
|---|---|---|---|---|---|
| | A | B | C | D | E |
| Alcohol or alcohol mixture | 55.0 | 60.0 | 70.0 | 80.0 | 90.0 |
| Polyethylene glycol homopolymer | 0.1 | 0.1 | 0.1 | 0.1 | 0.05 |
| Stabilizer | 0.2 | 0.2 | 0.2 | 0.2 | 0.1 |
| Surfactant or surfactant mixture | 3.0 | 3.0 | 4.0 | 4.0 | 3.0 |
| Water | 41.7 | 36.7 | 25.7 | 15.7 | 6.85 |

Foam compositions preferred according to the present invention for skin and hand disinfection (all data in wt % relative to the total quantity of the foam composition):

| | Example | | |
|---|---|---|---|
| | 1 | 2 | 3 |
| Ethanol | 55.0 | 80.0 | 90.0 |
| PEG-14M | 0.1 | 0.1 | 0.05 |
| Ethylcellulose | 0.2 | 0.2 | 0.1 |
| Bis-PEG/PPG-20/20 dimethicone | 3.0 | 4.0 | 3.0 |
| Demineralized water | 41.7 | 15.7 | 6.85 |

German patent application 10 2004 062 775.4 filed, Dec. 21, 2004, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. An alcoholic foamable composition, capable of forming a stabilized pump foam, comprising:
   a) 55 to 96 wt % of an alcohol or a mixture of alcohols of the general formula

R—OH wherein R denotes an aliphatic straight-chain or branched hydrocarbon group having 1 to 8 carbon atoms,
   b) 1 to 10 wt % of (i) at least one silicone surfactant or (ii) a mixture of fluoro and silicone surfactants, wherein the surface tension of (i) or (ii) is 20 to 40 dyn/cm,
   c) 0.05 to 2 wt % PEG polymer selected from the group consisting of PEG 7M to PEG 45M and mixtures thereof,
   d) 0.1 to 3 wt % of ethylcellulose polymer as foam stabilizer,
   e) optionally, at least one member selected from the group consisting of cosmetic auxiliaries, adjuvants, active ingredients, and mixtures thereof, and
   f) water, wherein the sum of components a) to f) is 100 wt % relative to the total quantity of the foamable composition, and wherein said alcoholic foamable composition is in the form of a pump-foam formulation before it is foamed, said pump-foam formulation being capable of forming a stabilized pump foam.

2. The alcoholic foamable composition according to claim 1, wherein component a) comprises at least one member selected from the group consisting of methanol, ethanol, 1-propanol, 2-propanol, 1-butanol, isobutyl alcohol, tert-butyl alcohol, the amyl alcohols, 1-petanol, 2-pentanol, 3-pentanol, neopentyl alcohol, 1-hexanol and mixtures thereof.

3. The alcoholic foamable composition according to claim 1, wherein component a) is ethanol.

4. The alcoholic foamable composition according to claim 1, wherein the surfactant consists of a silicone surfactant or a mixture of silicone surfactants.

5. The alcoholic foamable composition according to claim 1, which does not comprise a fluoro surfactant.

6. The alcoholic foamable composition according to claim 1, wherein component b) comprises a polysiloxane-polyether copolymer.

7. The alcoholic foamable composition according to claim 1, wherein component b) comprises a teraalkylammonium perfluoroalkylsulfonate.

8. A disinfectant, comprising the alcoholic foamable composition according to claim 1.

9. An antiseptic for wound, skin, stools and sputum disinfection or instrument disinfection, comprising the alcoholic foamable composition according to claim 1.

10. A laundry and surface disinfectant, comprising the alcoholic foamable composition according to claim 1.

11. A skin and hand disinfectant, comprising the alcoholic foamable composition according to claim 1.

12. An alcoholic foamable composition, capable of forming a stabilized pump foam, comprising:
 a) 55 to 96 wt %, relative to the total quantity of the foamable composition, of ethanol,
 b) 1 to 10 wt % of bis-PEG/PPG-20/20 dimethicone which is not fluorinated,
 c) 0.05 to 2 wt % PEG polymer selected from the group consisting of PEG 7M to PEG 45M and mixtures thereof,
 d) 0.1 to 3 wt % of ethylcellulose polymer,
 e) optionally, at least one member selected from the group consisting of cosmetic auxiliaries, adjuvants, active ingredients, and mixtures thereof, and
 f) water,
 wherein the surface tension of component b) lies in the range of ±15 dyn/cm of the surface tension of component a) or corresponds to the surface tension of component a), and
 wherein the sum of components a) to f) is 100 wt % relative to the total quantity of the foamable composition,
 wherein said alcoholic foamable composition is in the form of a pump-foam formulation before it is foamed, said pump-foam formulation being capable of forming a stabilized pump foam.

* * * * *